US006626931B2

(12) United States Patent
Milla et al.

(10) Patent No.: US 6,626,931 B2
(45) Date of Patent: Sep. 30, 2003

(54) IMPLANTABLE MEDICAL ELECTRONICS USING HIGH VOLTAGE FLIP CHIP COMPONENTS

(75) Inventors: Juan G. Milla, Mesa, AZ (US); Mark R. Boone, Mesa, AZ (US)

(73) Assignee: Medtronic, Inc., Minneapolis, MN (US)

( * ) Notice: Subject to any disclaimer, the term of this patent is extended or adjusted under 35 U.S.C. 154(b) by 191 days.

(21) Appl. No.: 09/748,598

(22) Filed: Dec. 26, 2000

(65) Prior Publication Data

US 2002/0082643 A1 Jun. 27, 2002

(51) Int. Cl.[7] .................................................. A61N 1/00
(52) U.S. Cl. ..................... 607/1; 607/5; 607/9; 607/36; 361/764
(58) Field of Search ............................... 607/1, 5, 9, 36, 607/37, 119, 2; 361/749, 764, 761

(56) References Cited

U.S. PATENT DOCUMENTS

| 5,776,797 A | 7/1998 | Nicewarner, Jr. et al. ... 438/107 |
|---|---|---|
| 5,954,751 A | 9/1999 | Chen et al. .................... 607/5 |
| 5,963,429 A | * 10/1999 | Chen ........................... 600/374 |
| 6,052,623 A | * 4/2000 | Fenner et al. ................. 607/36 |
| 6,121,676 A | 9/2000 | Solberg ....................... 257/686 |
| 6,146,743 A | * 11/2000 | Haq et al. ................... 428/210 |
| 6,156,028 A | * 12/2000 | Prescott ......................... 606/2 |
| 6,245,092 B1 | * 6/2001 | Schaldach, Jr. ................ 607/1 |

FOREIGN PATENT DOCUMENTS

| CH | 689 502 A5 | 5/1997 |
|---|---|---|
| EP | 0732124 A2 | 9/1996 |

\* cited by examiner

*Primary Examiner*—Mark Paschall
(74) *Attorney, Agent, or Firm*—Girma Wolde-Michael

(57) ABSTRACT

An implantable medical device having reduced volume includes a high voltage die mounted to a substrate and assembled into a device body. The die is flip chip mounted, reducing the size of the substrate and of the device. A high voltage implantable medical device such as an implantable cardio defibrillation device or a hybrid device has a high voltage flip chip die mounted to a substrate containing implantable medical device circuitry to operate with the high voltage flip chip.

8 Claims, 4 Drawing Sheets

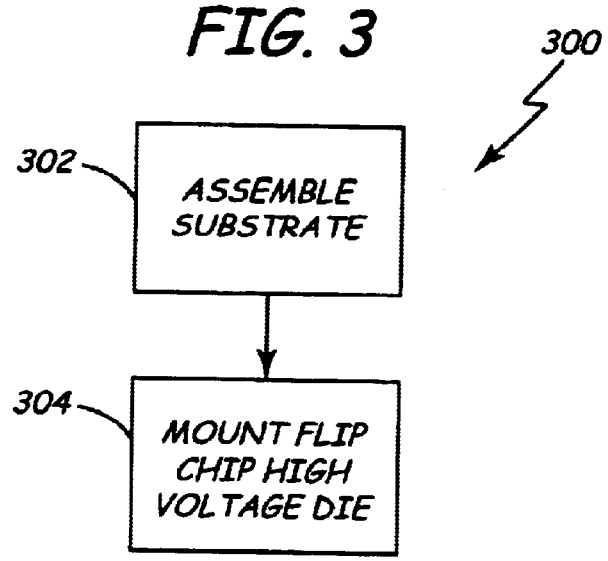
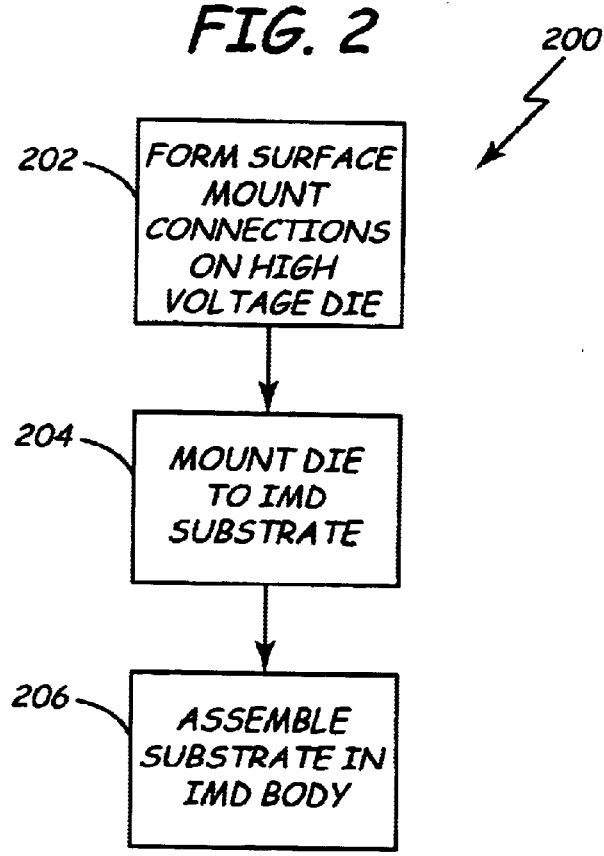

IMPLANTABLE MEDICAL ELECTRONICS USING HIGH VOLTAGE FLIP CHIP COMPONENTS

The present invention relates generally to implantable medical devices, and more specifically to such devices using high voltage flip chip components.

BACKGROUND OF THE INVENTION

Currently, nearly all high voltage integrated circuit mounting is accomplished with wire bonding. Typical high voltage dice have active terminations on both sides of the die. Wire bonding involves attaching one end of a thin wire to a termination point on a side of a die, attaching the other end of the thin wire to a pad on a substrate, and encapsulating the die and connection points in an encapsulant to prevent damage to the wire bond. Wire bonding has numerous problems. Some of the problems are, for example, wire bonds are fragile and require multiple connections that may also make a structure more fragile.

A typical wire bonded high voltage die package 100 is shown in top view in FIG. 1A and in side elevation view on FIG. 1B. Die package 100 includes a substrate 102, a die 104 having a top side 106 and a bottom side 108. The die 104 is attached to the substrate 102 by two types of connections, an epoxy 110 connection and two wire bond connections 112. The epoxy 110 connection is between the substrate 102 and the back side 108 of the die 104. The wire bond connections 112 include a connection of a wire 116 between a pad 114 on the top side 106 of die 104 and a pad 118 on the substrate 102.

Because of fragility and problems with arcing and wire damage and because the wires necessarily stick up from the die as shown in FIG. 1, once the die 104 is wire bonded on the top side 106 and the substrate 102, and conductively epoxied to the substrate on the back side 108, the entire area of the wire bonding connections 112 and die 104 is encapsulated. The encapsulation covers the entire area of the die, in addition to the entire area of the wire bond contact to the substrate, plus the vertical height of the wire off the die. The encapsulant die size is quite large.

As implantable medical devices become smaller and smaller, and as more and more components are added to such devices, the real estate available for components is shrinking. Components too are shrinking in size, but the need for improving the use of available volume and real estate continues.

In implantable medical devices, the footprints of dice and stacked dice packages typically exceed the bottom die size. For example, when wire bonding is used to electrically connect a die to rigid or flexible interposers, the package size is much larger than the bottom die size, and is therefore substantially size inefficient.

SUMMARY OF THE INVENTION

In one embodiment, a method for assembling an implantable medical device includes assembling a substrate containing circuitry for use in a medical device, and mounting a flip chip high voltage die to the substrate.

In another embodiment, a method for reducing the size of an implantable medical device includes preparing a high voltage device with terminations on a single side of the device die for surface mount technology application. The process includes preferably mounting the high voltage die on a reduced size implantable medical device substrate, and assembling the substrate into a reduced size body.

In yet another embodiment, an implantable medical device includes a body, a substrate, and a high voltage die mounted to the substrate using flip chip components. The high voltage die in one embodiment is a die such as that disclosed herein.

Other embodiments are described and claimed.

BRIEF DESCRIPTION OF THE DRAWINGS

FIG. 2 is a flow chart diagram of a method according to one embodiment of the present invention;

FIG. 3 is a flow chart diagram of a method according to another embodiment of the present invention;

DETAILED DESCRIPTION

Figure 1A:
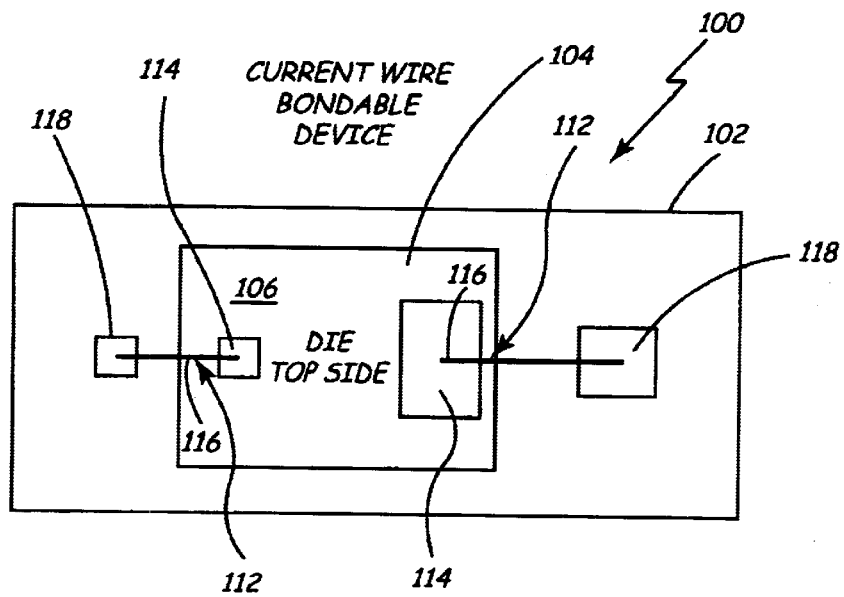
FIG. 1A is a top view of a wire bonded die.
Figure 1B:
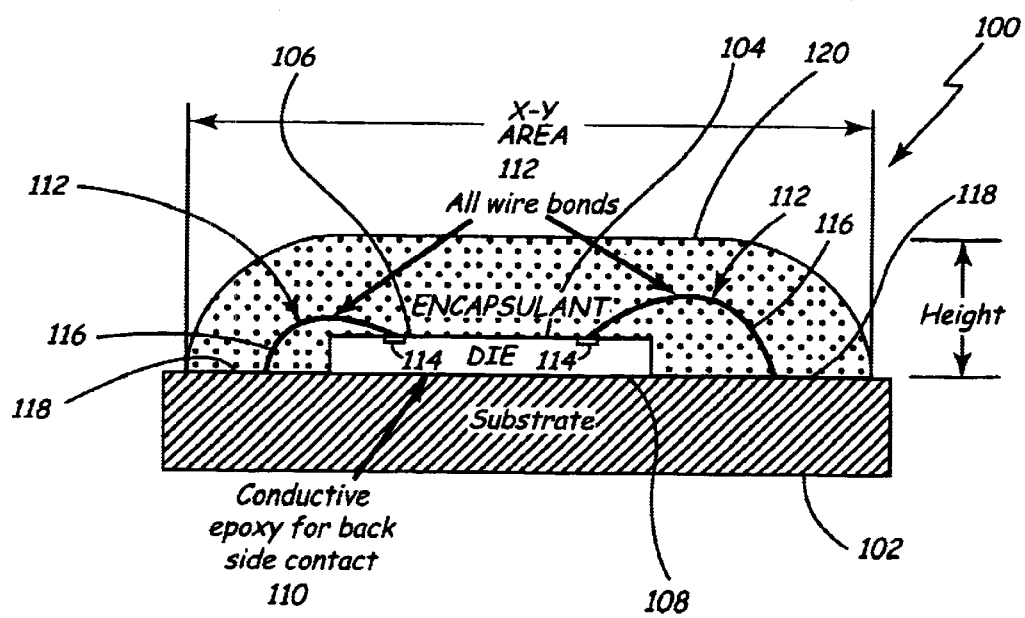
FIG. 1B is a side elevation view of a wire bonded die.

In the following detailed description of the embodiments, reference is made to the accompanying drawings which form a part hereof, and in which is shown by way of illustration specific embodiments in which the invention may be practiced. It is to be understood that other embodiments may be utilized and structural or logical changes may be made without departing from the scope of the present invention.

A method 200 of assembling an implantable medical device with high voltage flip chip technology is shown in FIG. 2. Method 200 comprises forming a surface mount connection structure on a high voltage die in block 202, mounting a high voltage flip chip die to an implantable medical device substrate for high voltage application in the IMD in block 204, and assembling the substrate in an IMD structure in block 206. As has been mentioned, such an IMD includes in various embodiments a defibrillator, a hybrid device for multiple medical device operations including high voltage operations, and the like.

High voltage flip chip dice used in one embodiment of the present invention have all of their connection terminations on a single side of the die. For example, all of the connections for the die to be connected to a substrate are present on one surface. In this embodiment, the die is then mounted using surface mount technology. The use of surface mount technology allows smaller amounts of real estate to be used in the mounting of the die.

In one embodiment, standard surface mount processes are used to form the surface mount structure on the high voltage flip chip die. Those processes, including under bump metalization (UBM) processes are well known in the art and will not be described further herein. Further, while a single die is discussed herein, many high voltage dice of varying types and families, including by way of example only and not by way of limitation, silicon controlled rectifiers (SCRs), insulated gate bipolar transistors (IGBTs), field effect transistors (FETs), and the like are amenable to the apparatuses and processes described herein, and are within the scope of the invention. Such high voltage devices for the purposes of this disclosure are devices producing voltages on the order of 100 volts or more.

FIG. 3 shows a method 300 for assembling an implantable medical device, comprising assembling a substrate containing medical device circuitry), in block 302, and mounting a flip chip high voltage die to the substrate in block 304. In various embodiment, the implantable medical device is a defibrillator, a hybrid device, or another implantable device with high voltage component requirements.

Figure 4:
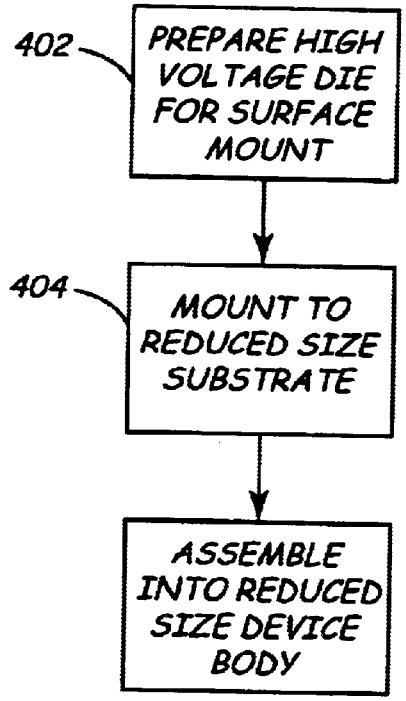
FIG. 4 is a flow chart diagram of a method according to yet another embodiment of the present invention.

A method 400 for reducing the size of an implantable medical device is shown in FIG. 4. Method 400 comprises in one embodiment preparing a high voltage device with terminations on a single side of the device die for surface mount technology application in block 402, mounting the high voltage die on a reduced size implantable medical device substrate in block 404, and assembling the substrate into a reduced size body in block 406.

In various embodiments, the implantable medical devices of the present invention use high voltage components for various purposes. Those purposes include by way of example implantable cardio defibrillation devices (ICDs), combination or hybrid pacing and defibrillating devices, and the like. As the implantable medical device industry continues to grow and diversify, the applications for high voltage components continue to increase as well. Since implantable medical devices use more and more components, in the face of consistent need for smaller sizes, high voltage flip chip devices become indispensable in reducing space-volume requirements.

The various method embodiments of the present invention, such as methods 200, 300, and 400 reduce the size of a high voltage die. Typical high voltage dice formed with wire bonding techniques have a vertical height on the order of 60 to 70 mils exclusive of the substrate. Flip chip dice, on the other hand, have a vertical height on the order of 20 mils exclusive of the substrate. Typical wire bonded devices when mounted to substrates cover an area of horizontal real estate on the order of twice or more the area of flip chip devices. High voltage flip chip devices therefore reduce overall volume used in ever-shrinking implantable medical devices by an average of 50 percent or more over wire bonded devices. The additional real estate and volume allows implementation of additional components increasingly necessary in all implantable medical devices, especially in hybrid devices that perform multiple functions.

Figure 5:
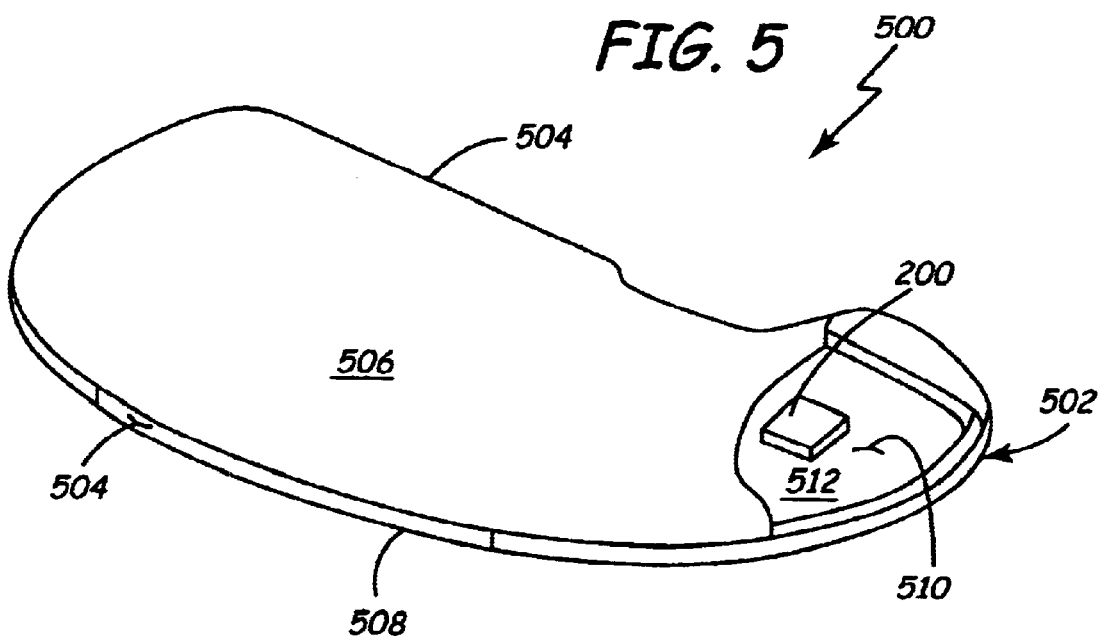
FIG. 5 is a view of an implantable medical device according to another embodiment of the present invention.

FIG. 5 shows an embodiment of an implantable medical device 500. The type of implantable medical device will vary depending upon its function, as will the shape of the IMD 500, without departing from the scope of the invention. IMD 500 includes body 502 having edges 504 top 506 and bottom 508. The interior chamber 510 of the implantable medical device 500 is the location for the internal components of the IMD 500 including substrate 512. Such components may include but are not limited to high voltage devices such as dice 200 mounted to the substrate 512, telemetry devices, pacing circuitry, control circuitry, batteries, and the like. The circuits within the IMD are typically integrated circuits formed on or mounted to a substrate.

Figure 6:
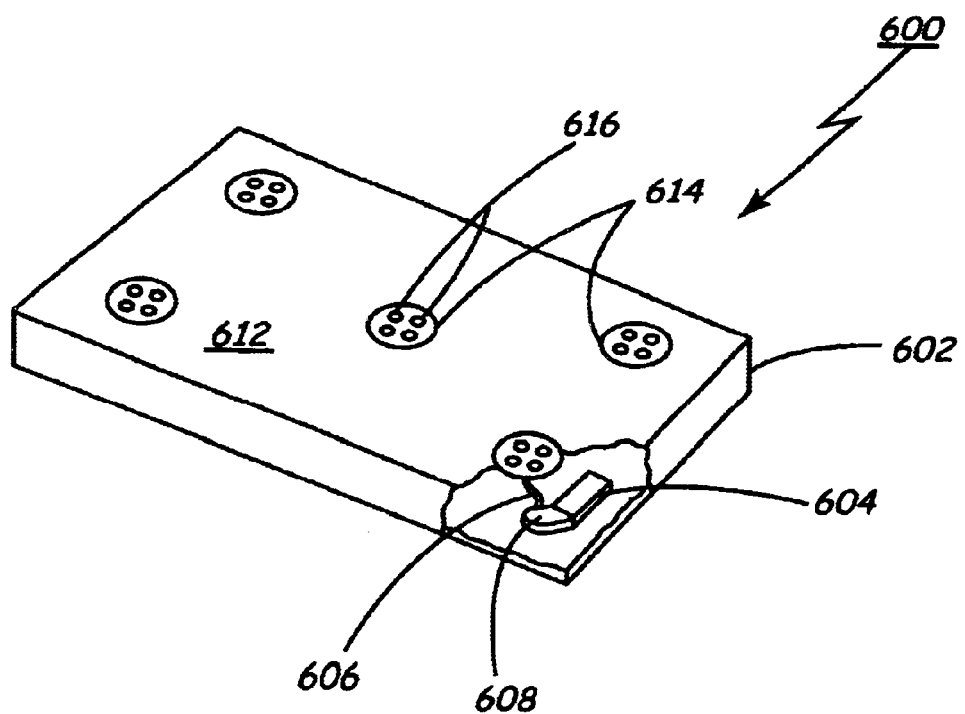
FIG. 6 is a partial cutaway perspective view of a high voltage die.

An example of a high voltage chip is shown in FIG. 6. Such a high voltage die is suitable for mounting in the various embodiments of the present invention, such as ICDs, hybrid devices, and the like. A typical die 600 comprises die chip 602 on which or in which are formed a plurality of components 604. Components 604 typically include high voltage components. All of the terminations are in this die on a single side 612 of the die 600. A routing structure 406 within the die chip 602 routes active terminations 608 to side 612 of the die 600. Base pads 614 for surface mount structures serve as the platform for creating flip chip connections of the rerouted active terminations to a substrate. Flip chip bumps 616 are applied to the die in standard fashion.

While specific mention has been made herein of ICDs or hybrid devices containing circuitry and components for pacing as well as high voltage operations such as defibrillation, the implantable medical device industry is constantly evolving. Specifically, devices are becoming more and more sophisticated. For example, the direction the industry is moving toward hybrid devices, that are capable of performing multiple different implantable device functions such as defibrillation, pacing, and the like. Such hybrid devices use high voltage components, and the methods and apparatuses of the present invention are amenable to use in such hybrid devices. While the descriptions herein have been made generally with respect to ICDs and hybrid devices, any implantable medical device using high voltage therapy is amenable to the methods and apparatuses described herein.

Advantages of the present invention include by way of example only and not by way of limitation reduction in the size of high voltage implantable medical devices, not only in length and width, but also in height. Total volume reduction is on the order of 50 percent or more. The reduction in size is achieved because the flip chip technology does not require the extra encapsulant area and height of wire bonding.

Further advantages include reduction in fully allocated product cost because flip chip mounting is less expensive than wire bonding. Flip chip mounting reduces tool requirements, because no wire connections need to be made, and no encapsulant is required. Further, flip chip mounting reduces direct labor due to the reduced number of manufacturing processes involved in flip chip mounting and preparation. Manufacturing of flip chip devices is faster than the manufacture of wire bond devices because manufacturing is accomplished in fewer steps.

Still further advantages include improved quality and reliability by creating more robust and consistently repeatable high quality interconnect products, and the like. Furthermore, cycle time is reduced not only because fewer process steps are required for assembling IMDs, but because the steps themselves are accomplished faster. For example, the elimination of the encapsulant not only provides manufacturing advantages, but also reduces process time because the waiting period for curing is eliminated.

While the various embodiments of the present invention have been described with respect to implantable medical devices, the embodiments of are amenable to use in any high voltage component product with size limitations and a need for simple manufacturing processes, including but not limited to hearing aids and the like.

It is to be understood that the above description is intended to be illustrative, and not restrictive. Many other embodiments will be apparent to those of skill in the art upon reading and understanding the above description. The scope of the invention should, therefore, be determined with reference to the appended claims, along with the full scope of equivalents to which such claims are entitled.

What is claimed is:

1. An implantable medical device, comprising:
    a body having an interior chamber;
    a substrate mounted in the interior chamber; and
    a flip chip high voltage die mounted to the substrate, said flip chip die comprising at least one high voltage active device operable at a voltage level of at least 100 volts.

2. The implantable medical device of claim 1, wherein the high voltage die comprises:

a flip chip mounting structure formed on a single side of the die.

3. The implantable medical device of claim 1, wherein the implantable medical device is a defibrillator.

4. The implantable medical device of claim 1, wherein a hybrid circuit is mounted in the interior chamber.

5. A method for assembling a defibrillator, comprising:

providing a body having an interior chamber;

providing a substrate;

mounting a flip chip high voltage die to the substrate, said die comprising at least one high voltage active device operable at a voltage level of at least 100 volts; and mounting the substrate in the interior chamber.

6. A method of packaging high voltage chips in an implantable medical device, comprising:

forming a high voltage flip chip die comprising at least one high voltage active device operable a voltage level of at least 100 volts; and mounting the high voltage flip chip die to a substrate.

7. A method for assembling an implantable medical device, comprising:

forming a high voltage flip chip die comprising at least one high voltage active device operable at a voltage level of at least 100 volts;

mounting the high voltage flip chip die to a device substrate; and assembling the substrate in a device body.

8. The method of claim 7, wherein the high voltage flip chip die is mounted to the device substrate by surface mounting technology.

* * * * *